United States Patent [19]

Friese et al.

[11] Patent Number: 5,486,279

[45] Date of Patent: Jan. 23, 1996

[54] ELECTROCHEMICAL MEASURING PROBE

[75] Inventors: Karl-Hermann Friese, Leonberg; Helmut Weyl, Schwieberdingen; Hans-Martin Wiedenmann, Stuttgart, all of Germany

[73] Assignee: Robert Bosch GmbH, Stuttgart, Germany

[21] Appl. No.: 227,568

[22] Filed: Apr. 14, 1994

Related U.S. Application Data

[63] Continuation of Ser. No. 842,378, filed as PCT/DE90/00746, Sept. 29, 1990.

[30] Foreign Application Priority Data

Oct. 17, 1989 [DE] Germany .................... 39 34 586.6

[51] Int. Cl.⁶ .................................................. G01N 27/407
[52] U.S. Cl. ............................................ 204/429; 204/427
[58] Field of Search ....................... 204/153, 18, 421–429

[56] References Cited

U.S. PATENT DOCUMENTS

| | | | |
|---|---|---|---|
| 4,021,326 | 5/1977 | Pollner et al. ........................ | 204/429 |
| 4,164,462 | 8/1979 | Ichikawa et al. ..................... | 204/429 |
| 4,177,112 | 12/1979 | Suzuki et al. ........................ | 204/429 |
| 4,292,158 | 9/1981 | Muller et al. ........................ | 204/429 |
| 4,296,148 | 10/1981 | Friese .................................. | 204/426 |
| 4,354,912 | 10/1982 | Friese .................................. | 204/426 |
| 4,402,820 | 9/1983 | Sano et al. ............................ | 204/429 |
| 4,502,939 | 3/1985 | Holfelder et al. .................... | 204/429 |

*Primary Examiner*—T. Tung
*Attorney, Agent, or Firm*—Spencer & Frank

[57] ABSTRACT

An electrochemical measuring probe for determining the oxygen content of gases, in particular of exhaust gases of internal combustion engines, whose measuring probe body consists essentially of a solid electrolyte, for example stabilised $ZrO_2$ and whose electrode exposed to the gas to be measured is a cermet electrode which is coated with a finely porous ion-conducting covering layer composed of an ion-conducting supporting matrix material having no sintering activity of the type standard for cermet electrodes the covering layer is covered by a porous protective layer. The ion-conducting porous covering layer appreciably increases the activity of the cermet electrode.

8 Claims, 1 Drawing Sheet ically applies to electrochemical measuring probes with a
ELECTROCHEMICAL MEASURING PROBE This application is a Continuation, of application Ser. No. 07/842,378, filed as PCT/DE90/00746, Sept. 29, 1990.

BACKGROUND OF THE INVENTION

The invention is based on an electrochemical measuring probe for determining the oxygen content of gases as defined by the generic class of the main claim.

To determine the oxygen content of gases, in particular of exhaust gases of internal combustion engines, it is generally known, for example from German Patent Specifications 2,206,216, 2,852,638 and 2,619,746 and from German Offenlegungsschrift 2,913,633, to use electrochemical measuring probes—often also referred to as gas sensors—comprising a solid electrolyte, for example stabilised zirconium dioxide, a first electrode on the side of the solid electrolyte exposed to the gas to be measured, a second electrode on the side of the solid electrolyte exposed to a comparison gas of known oxygen content and a porous ceramic protective layer on the first electrode, which is exposed to the gas to be measured.

From German Patent Specification 2,852,638 and German Offenlegungsschrift 2,913,633, it is furthermore known to use, as electrodes exposed to the gas to be measured, electrodes composed of a finely divided ceramic material to form a supporting matrix and a finely divided electron-conducting material, so-called cermet electrodes. In this connection, the finely divided ceramic material used to form the supporting matrix may consist, for example, of stabilized zirconium dioxide or aluminium oxide, and the finely divided electron-conducting material, for example, of platinum, a platinum alloy, for example platinum-rhodium alloy, or a palladium-noble metal alloy.

From German Patent Specification 2,852,638, it is furthermore known to produce the measuring probe body from partially stabilized zirconium dioxide and the supporting matrix of the cermet electrode from fully stabilized zirconium dioxide.

From German Offenlegungsschrift 3,737,215, it is furthermore known to deposit a porous ceramic protective layer composed of an $Al_2O_3$— and/or Mg-spinel $(MgO.Al_2O_3)$-matrix with $ZrO_2$ particles included therein on the electrode exposed to the gas to be measured.

Finally, from German Offenlegungsschrift 3,735,298 it is known to deposit a densely sintering covering layer composed of the raw material mixture of the probe-base ceramic having the same or increased sintering activity on the supply lead of the electrode, exposed to the gas to be measured, of an electrochemical measuring probe having a probe base formed from a solid electrolyte. This covering layer has the advantage that it can be applied to the conductor track before the sintering process and screens the conductor track so hermetically that a trouble-free continuous operation of the measuring probe is possible even in very rich exhaust gases ($\lambda \leq 0.8$) at high temperatures with heavy soot formation.

SUMMARY AND ADVANTAGES OF THE INVENTION

According to the invention an electrochemical measuring probe is provided for determining the oxygen content of gases, in particular of exhaust gases of internal combustion engines, which probe comprises a solid-electrolyte body having at least one cermet electrode on the side of the solid-electrolyte body exposed to the gas to be measured, with the electrode having a supporting matrix composed of a finely divided ion-conducting ceramic material, a porous ceramic protective layer on the cermet electrode exposed to the gas to be measured, and a finely porous ion-conducting covering layer disposed between the cermet electrode and the porous ceramic protective layer, with the finely porous ion-conducting covering layer consisting, at least predominantly, of an ion-conducting supporting matrix material, preferably having no sintering activity, of the type standard for cermet electrodes.

Compared with the known electrochemical measuring probes of the prior art, an electrochemical measuring probe having the features according to the invention has the advantage of an increased electrode activity. The finely porous covering layer provided according to the invention results in an optimum formation of the 3-phase boundary even in the interface of the cermet electrode situated on the outside. The conversion of the exhaust-gas or reference-gas components is consequently ensured even in this electrode region, which is most closely adjacent to the outer gas space and is consequently the most loaded catalytically and electrochemically.

The electrochemical measuring probe according to the invention consequently differs from the known electrochemical measuring probes of the general type including a solid-electrolyte body, at least one cermet electrode, having a supporting matrix composed of a finely divided ion-conducting ceramic material, disposed on the side of the solid electrolyte body exposed to the gas to be measured, and a porous ceramic cover layer on the cermet electrode exposed to the gas to be measured, as a result of the additional deposition of a covering layer on the cermet electrode exposed to the gas to be measured and is composed of an ion-conducting material, preferably having no sintering activity, such as is normally used to form the supporting matrix of cermet electrodes.

The electrochemical measuring probes according to the invention may consequently be ones with a tubular probe base or, alternatively, also a planar measuring probes.

This means that the measuring probe body, for example the tubular probe base, may consist of one of the solid electrolytes normally used to produce electrochemical measuring probes. According to an advantageous development of the invention, the measuring probe body consists of a ceramic material with a $ZrO_2$ base, in particular stabilized $ZrO_2$, for example of the type disclosed by German Offenlegungsschrift 2,810,134.

The electrodes of the electrochemical measuring probe according to the invention may have the standard known construction. The cermet electrode exposed to the gas to be measured may consequently consist, for example, of a standard Pt-cermet or Pt-alloy-cermet electrode. The supporting matrix material of these cermet electrodes may consist, for example, of stabilized $ZrO_2$, but the degree of stabilized of the $ZrO_2$ used to form the cermet electrode may possibly differ from the degree of stabilized of the $ZrO_2$ used to produce the measuring probe body, as is known from German Patent Specification 2,852,638.

To form the covering layer, any desired ion-conducting supporting matrix material having no sintering activity can be used, as is normally used to form the supporting matrix of cermet electrodes. According to an advantageous development of the invention, to produce the covering layer, the same supporting matrix material having no sintering activity is used which is also used to produce the cermet electrode exposed to the test gas of the electrochemical measuring probe according to the invention. Preferably, at least 80% by volume of the covering layer consists of the ion-conducting supporting matrix material having no sintering activity. This means that the covering layer may, for example, consist of partially or completely stabilized $ZrO_2$ and, furthermore, of partially or completely stabilized $HfO_2$ or of partially or completely stabilized $Bi_2O_3$.

In addition to the ion-conducting component having no sintering activity, such as for example the partially or completely stabilized $ZrO_2$, the covering layer may, for example, contain still other temperature-resistant oxides, such as $Al_2O_3$, Mg spinel and/or mullite.

The thickness of the covering layer may vary. Advantageously, it is at least ½ as thick as the cermet electrode and is not more than 3 times as thick as the cermet electrode. This means that the covering layer has a thickness of, preferably, 2.5 to 30 μm.

The covering layer may be deposited on the cermet electrode by standard known application techniques, for example by standard known printing, immersing and spraying methods, in particular before or after the final sintering of the measuring probe body.

The term "finely porous" means that the porosity of the covering layer corresponds to that of the cermet electrode or is at least very similar to it and that the pore diameters are not larger than the layer thickness of the covering layer.

Typically, to form the covering layer, a coating compound is used which consists of:

(a) 30 to 65% by weight of covering-layer raw-material mixture consisting of solid-electrolyte oxide and stabilizer oxide and, optionally, of a flux additive;

(b) 0.5 to 7.5% by weight of an organic binder, and (c) 30 to 68% by weight of solvent, optionally containing additives such as wetting agents, foam inhibitors, dispersants and/or suspension agents.

After applying the covering layer and sintering it on, the porous protective layer, which may consist in the standard known manner, for example, of an $Al_2O_3$— and/or Mg-spinel layer and can be applied by plasma-jet spraying technology is applied.

BRIEF DESCRIPTION OF THE DRAWINGS

The drawings serve to explain the invention in greater detail. In them

DETAILED DESCRIPTION OF THE PREFERRED EMBODIMENT

Figure 1:
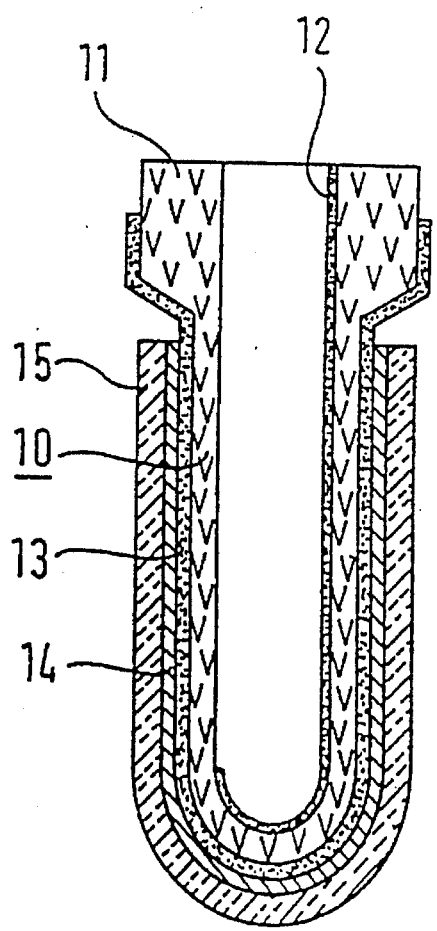
FIG. 1 shows the head of an electrochemical measuring probe in section.
Figure 2:
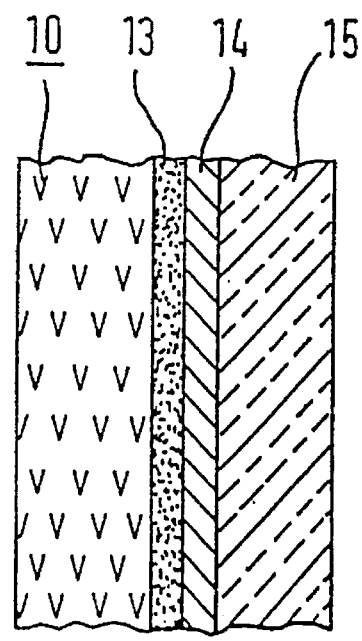
FIG. 2 shows a detail of the measuring probe according to FIG. 1 on an enlarged scale.

The measuring probe head consists of a tube 10 closed at one end and consisting of a solid electrolyte, for example stabilized zirconium dioxide, its open end 11 having an increased wall thickness. On the inside wall of the tube 10 in the air reference channel is the inside electrode 12, for example composed of 60% by volume of a palladium-platinum alloy containing 2% by volume of platinum and 40% by volume of stabilized zirconium dioxide. On the outside wall of the tube 10 is the cermet electrode 13 exposed to the test gas and, for example, composed of 60% by volume of platinum and 40% by volume of stabilized zirconium dioxide, with the finely porous ion-conducting covering layer 14 thereon and the porous ceramic protective layer 15 on top of the latter. The measuring probe head shown is part of a standard electrochemical measuring probe such as is described, in principle, in greater detail, for example in German Patent Specification 2,913,633.

EXAMPLE

The solid-electrolyte body was prepared from a partially stabilized zirconium oxide ceramic composed of 95 mol-% $ZrO_2$ and 5 mol-% $Y_2O_3$ with 3% by weight of $Al_2O_3$ added and was presintered for two hours at 1,100° C. The cermet electrode 13 was produced from a suspension containing 60% by volume of platinum and 40% by volume of a $Y_2O_3$-stabilized zirconium oxide powder composed of a raw-material mixture of 92.5 mol-% $ZrO_2$ and 7.5 mol-% $Y_2O_3$, with 4% by weight of $Al_2O_3$ added. The ceramic components were pre-ground in the dry state to a specific surface of 11 $m^2/g$ and then ground together with the platinum powder using a thinning oil in a centrifugal ball mill. This suspension was then deposited on the presintered solid-electrolyte sensor body in a known manner by spraying-on, brushing-on, rolling-on, immersion, rolling,. casting or printing in a layer thickness of 10 to 30 μm and dried.

Starting from a coating compound composed of a raw-material mixture of 92.5 mol-% $ZrO_2$ and 7.5 mol-% $Y_2O_3$, with 4% by weight of $Al_2O_3$ added, the ion-conducting, porously sintering covering layer 14 was deposited on the cermet electrode by spraying-on, brushing-on or printing-on in a layer thickness of 5 to 15 μm. The coated solid-electrolyte body was then subsequently sintered in an oxidising atmosphere at 1,500° C. with a soaking time of 5 hours. A porous ceramic protective layer 15 composed of Mg-spinel powder was then additionally deposited on the covering layer by plasma-jet spray.

In comparison measurements, the measuring probe produced in this way exhibited an adequate sensor function even from an exhaust gas temperature of 285° C. upwards, whereas this was achieved by sensors without the electrode covering layer according to the invention only above 330° C.

We claim:

1. Electrochemical measuring probe for determining the oxygen content of gases comprising: a solid-electrolyte body having at least one cermet electrode on the side of the solid-electrolyte body exposed to the gas to be measured with said at least one electrode having a supporting matrix composed of a finely divided ion-conducting ceramic material, a porous ceramic protective layer on the cermet electrode exposed to the gas to be measured, and a finely porous ion-conducting covering layer disposed between and directly adherent to the cermet electrode and the porous ceramic protective layer; and wherein the finely porous ion-conducting covering layer is comprised predominately of the same ion-conducting supporting matrix material as that of the cermet electrode exposed to the gas to be measured, with the porosity of said covering layer being substantially the same as that of said cermet electrode, with said covering layer being at least ½, and not greater than 3 times, as thick as said at least one cermet electrode, and with the pore diameters in said covering layer being not larger than the layer thickness of said covering layer.

2. Measuring probe according to claim 1, wherein the finely porous covering layer comprises at least 80% by volume of the same ion-conducting supporting matrix material as said at least one cermet electrode.

3. A measuring probe according to claim 2, wherein said finely porous ion-conducting supporting material of said covering layer has no sintering activity.

4. Measuring probe according to claim 1 wherein the supporting matrix material of said covering is comprised of stabilized zirconium dioxide.

5. A measuring probe according to claim 4, wherein said finely porous ion-conducting supporting material of said covering layer has no sintering activity.

6. Measuring probe according to claim 1, wherein the supporting matrix material of said covering is comprised of completely stabilized zirconium dioxide.

7. A measuring probe according to claim 6, wherein said finely porous ion-conducting supporting material of said covering layer has no sintering activity.

8. A measuring probe according to claim 1, wherein said finely porous ion-conducting supporting material of said covering layer has no sintering activity.

* * * * *